United States Patent [19]

Mazziotta et al.

[11] Patent Number: 5,008,546
[45] Date of Patent: Apr. 16, 1991

[54] INTRAOPERATIVE BETA PROBE AND METHOD OF USING THE SAME

[75] Inventors: John C. Mazziotta, Beverly Hills, Calif.; Farhad Daghighian, New York, N.Y.; Edward J. Hoffman, Van Nuys, Calif.

[73] Assignee: The Regents of the University of California, Oakland, Calif.

[21] Appl. No.: 539,794

[22] Filed: Jun. 18, 1990

[51] Int. Cl.⁵ .................. G01T 1/161; G01T 1/20; G01T 1/203
[52] U.S. Cl. .................................. 250/366; 250/367
[58] Field of Search ............... 250/366, 367, 308, 303, 250/486.1, 482.1, 370.11; 128/654

[56] References Cited
U.S. PATENT DOCUMENTS 4,267,446  5/1981  Brown et al. ................. 250/394

OTHER PUBLICATIONS

Hickernell, T. et al., "Dual-Detector Probe for Surgical Tumor Staging", J. Nucl. Med. vol. 29, No. 6, Jun. 1988.

Primary Examiner—Jack I. Berman
Assistant Examiner—Richard Hanig
Attorney, Agent, or Firm—Beehler & Pavitt

[57] ABSTRACT

An intraoperative radiation probe is devised to detect radiolabelled malignant tissues by being selectively sensitive to beta radiation while insensitive to gamma radiation. The probe is comprised of two plastic scintillators optically coupled to corresponding photomultiplier tubes via corresponding light pipes. One of the plastic scintillators is shielded against beta radiation while the other is left to detect both beta and gamma radiation. The gamma radiation sensitivity of the dual probes is empirically established and used as a weighted factor to subtract the outputs of the two probes to leave a signal indicative of the beta radiation emitted by the radiolabelled tissue. Because of the shorter range of beta radiation within tissue, only near radiolabelled tissue is detected by the probe while strongly radiolabelled, more distant tissues exposing the probe to gamma radiation are ignored. The reliably identified near radiolabelled tissues can then be surgically removed. The probe is usable in any application where local beta radiation is to be differentiated from other types and sources of radiation.

20 Claims, 5 Drawing Sheets

INTRAOPERATIVE BETA PROBE AND METHOD OF USING THE SAME

BACKGROUND OF THE INVENTION

1. Field of the Invention

The invention relates to the field of radiation detection probes and in particular to a beta or positron probe used during surgery to intraoperatively detect tissue labelled with positron or electron emitting isotopes.

2. Description of the Prior Art

The goal of oncological surgery is to completely remove neoplastic cells while sparing adjacent normal cells. This surgery is often either impossible or fails because the tumor has infiltrated the tissue to form small fingers which cannot be detected by visual examination or numerous small tumors which are dispersed throughout a large area of tissue. Failure to remove such diseased tissue often only leads to a continuation or recurrence of the cancer.

Radiolabelled monoclonal antibodies and other radiopharmaceuticals have been developed which preferentially bind to cancer cells. Detection and removal of these radioactively tagged cancer cells increases the success rate of such surgeries and can be realized if the tagged cells can be accurately located.

Prior art attempts to develop intraoperative probes for tumor location are limited in their usefulness because of their high sensitivity to gamma radiation. The range of gamma radiation in body tissue is large and therefore accumulations of the radioactive marker in a distant organ can create a high background gamma radiation making the detection of nearby tagged tissues difficult or impossible.

One prior art attempt to distinguish marked near tissues from marked distant tissues is shown by Hickernell, "Dual-Detector Probe for Surgical Tumor Staging", The Journal of Nuclear Medicine, Vol. 29, No. 6, June 1988, pages 1101-1106. Hickernell shows a dual probe which simultaneously monitors gamma counts from a possible tumor site along with counts from adjacent normal tissue using two concentric, collimated scintillation detectors. A comparison of the counts between the central axial and concentric detectors is used to distinguish a small tumor, which is directly in front of the probe, from tissue sources generating background activity. Hickernell has a first scintillation detector axially disposed in the probe with a second scintillation detector coaxially disposed about the first detector. Two lead collimators extend forwardly of the scintillation detectors. Like the detectors, the lead collimators are coaxially concentric with each other so that the two collimators divide the radiation incident of the end of the probe between the center axial detector and circumferential coaxial detector.

The theory is that a distant source of radiation will uniformly radiate both the center and circumferential detectors and that a close source of radiation, if placed in line with and laterally extending no more than the diameter of the center collimator will provide radiation predominately to the center detector. The difference in radiation received between the center detector and the circumferential detector is determined to identify a radiolabelled small tumor immediately in front of the center collimator of the probe.

The limitation of Hickernell's device is that if the near tissue source of the radiation is larger than the aperture area of the central collimator of the probe, it will provide radiation to both the circumferential detector as well as the center detector. The probe will therefore be blind to near tumors larger than the size of the central collimator aperture. Furthermore, it should be noted that Hickernell's device is a gamma detector and has no ability whatsoever to preferentially detect beta particles. Hickernell's device is sensitive to any background gamma radiation noise that my exist.

Heretofore, beta radiation has not been significantly used in medical applications since the range of beta particles within tissue is relatively short, typically from a micron to a few millimeters depending upon the energy of the particle. In particular, positron emitters have rarely been used since the half life of biologically useful positron emitters is fairly short, typically between an order of a few seconds to a 100 minutes. However, the recent common establishment of cyclotron facilities at advanced medical centers throughout the world has provided a practical opportunity for the production of such short half-life beta markers. The positron emitter is manufactured at the cyclotron and used on site or at a location which is within one to two hour's shipment time of the cyclotron site.

Positron emitters have the advantage that many of the natural organic elements which occur in the body in abundance have emitting isotopes analogs, have high energies, short half-lives which reduce post operative tissue handling and disposal radiation hazards.

Phosphorous 32, for example, a high energy beta emitter, has been used in the prior art to mark brain tumor tissue and has been successfully detected with a semiconductor detector. Phosphorous 32 is advantageous in that it generates high energy beta radiation with no gamma radiation. The problems dealt with in Hickernell therefore do not occur since there is no background gamma radiation. However, the applicability of phosphorous 32 as a marker is limited because it does not localize well in some tissues such as gliomas, it has a long half-life and is toxic to bone marrow.

Therefore, it is anticipated that if beta radiation is to be used as a tissue marker, some type of apparatus and methodology must be devised to detect the beta radiation notwithstanding the existence of background gamma radiation generated by the normally used types of radioactive markers.

BRIEF SUMMARY OF THE INVENTION

The invention is a probe system for preferentially detecting beta radiation over background gamma radiation from a source of beta and gamma radiation. The system comprises a first element for detecting beta and gamma radiation at an arbitrarily selected location. A second element selectively detects only one type of radiation of the beta and gamma radiation. The second and first element are coupled together.

As a result, beta radiation from near sources is reliably differentiated from gamma radiation emitted from far sources.

In one embodiment the first element comprises a scintillation detector and the second element comprises a circuit for adjusting the detection threshold energy of the scintillation detector above the Compton edge of the source of beta and gamma radiation.

In the preferred embodiment the first element comprises a first scintillation detector arranged and configured to detect beta and gamma radiation from the source. Note that the scintillator is much more efficient for beta than for gamma radiation. The second element comprises a second scintillation detector for detecting only gamma radiation from the source, and comprises an element for generating a weighted difference between the outputs of the first and second detectors. The difference is representative of beta radiation detection by the probe system.

The second scintillation detector is identical to the first scintillation detector and further comprises an element for shielding the second scintillation detector from beta radiation.

The element for shielding the second scintillation detector is a conductive covering of a predetermined thickness sufficient to absorb substantially all beta radiation emitted by the source.

The scintillation detector comprises a plastic scintillator; a light tube optically coupled to the plastic scintillator; and a circuit for converting light received through the light tube from the plastic scintillator into an electrical signal.

In particular the scintillation detector comprises a plastic scintillator, a light tube optically coupled to the plastic scintillator, and a circuit for converting light received through the light tube from the plastic scintillator into an electrical signal.

The probe system further comprises an element for rendering the plastic scintillator light tight without substantial interference to penetration of beta and gamma radiation into the plastic scintillator.

The invention is also characterized as a dual probe system for preferentially detecting beta radiation emitted by radiopharmaceutically marked tissue marked with isotopes emitting beta and gamma radiation in intraoperative surgery. The dual probe comprises a first detector for detecting beta and gamma radiation, a second detector for detecting gamma radiation, and an element for subtracting a weighted value of the output of the second detector from the output of the first detector to derive a signal indicative of beta radiation detected from the tissue by the dual probe system.

As a result, the location of radioactively tagged tissues may be reliably and accurately identified utilizing beta radiation without contamination from gamma radiation originating in adjacent tissues.

The first and second detectors further comprise a first and second corresponding photomultiplier tube for generating an electrical signal in response to an optical input. A light tube couples scintillation events within the first and second plastic scintillators to the first and second photomultiplier tube element respectively.

The second detector comprises an element for shielding the second detector from beta radiation.

The element for subtracting uses a weighted factor empirically determined by flooding the first and second detector with gamma radiation only and generating a ratio of their respective gamma radiation sensitivities.

The invention is still further characterized as a method for intraoperatively identifying the location of small masses of radioactively tagged tissues comprising the steps of detecting beta and gamma radiation from the tissue in a first detector. Gamma radiation from the tissue is simultaneously detected in a second detector at substantially the same location. The amount of beta and gamma radiation detected by the first detector is compared with the amount of gamma radiation detected by the second detector to generate a weighted difference of the amount of radiation detected by the first and second detectors representative of the amount of beta radiation emitted by the tissue.

As a result, small masses of tissue radioactively tagged with beta and gamma radiation isotopes may be detected near the location of the first and second detectors notwithstanding the presence of gamma radiation from the tissue more distantly located from the location.

The invention can be characterized as an improvement in a method for intraoperatively locating small masses of radioactively tagged tissues in the presence of radioactively tagged distant tissue masses each tagged with a radioactive isotope comprising the steps of providing a scintillation detector having a plastic scintillator capable of detecting beta and gamma radiation. The threshold energy detectable by the scintillation detector is adjusted to an energy threshold set at the Compton edge of the radioactive isotope.

As a result, radioactively beta emitting near tissue is differentiated from radioactively gamma emitting distant tissue.

The invention is better visualized by turning to the following drawings wherein like elements are referenced by like numerals.

The invention and its various embodiments may be better understood by now turning to the following detailed description.

DETAILED DESCRIPTION OF THE PREFERRED EMBODIMENTS

An intraoperative radiation probe is devised to detect radiolabelled malignant tissues by being selectively sensitive to beta radiation while insensitive to gamma radiation. The probe is comprised of two plastic scintillators optically coupled to corresponding photomultiplier tubes via corresponding light pipes. One of the plastic scintillators is shielded against beta radiation while the other is left to detect both beta and gamma radiation. The gamma radiation sensitivity of the dual probes is empirically established and used as a weighted factor to subtract the outputs of the two probes to leave a signal indicative of the beta radiation emitted by the radiolabelled tissue. Because of the shorter range of beta radiation within tissue, only near radiolabelled tissue is detected by the probe while strongly radiolabelled, more distant tissues exposing the probe to gamma radiation are ignored. The reliably identified near radiolabelled tissues can then be surgically removed.

Figures 1, 1A:
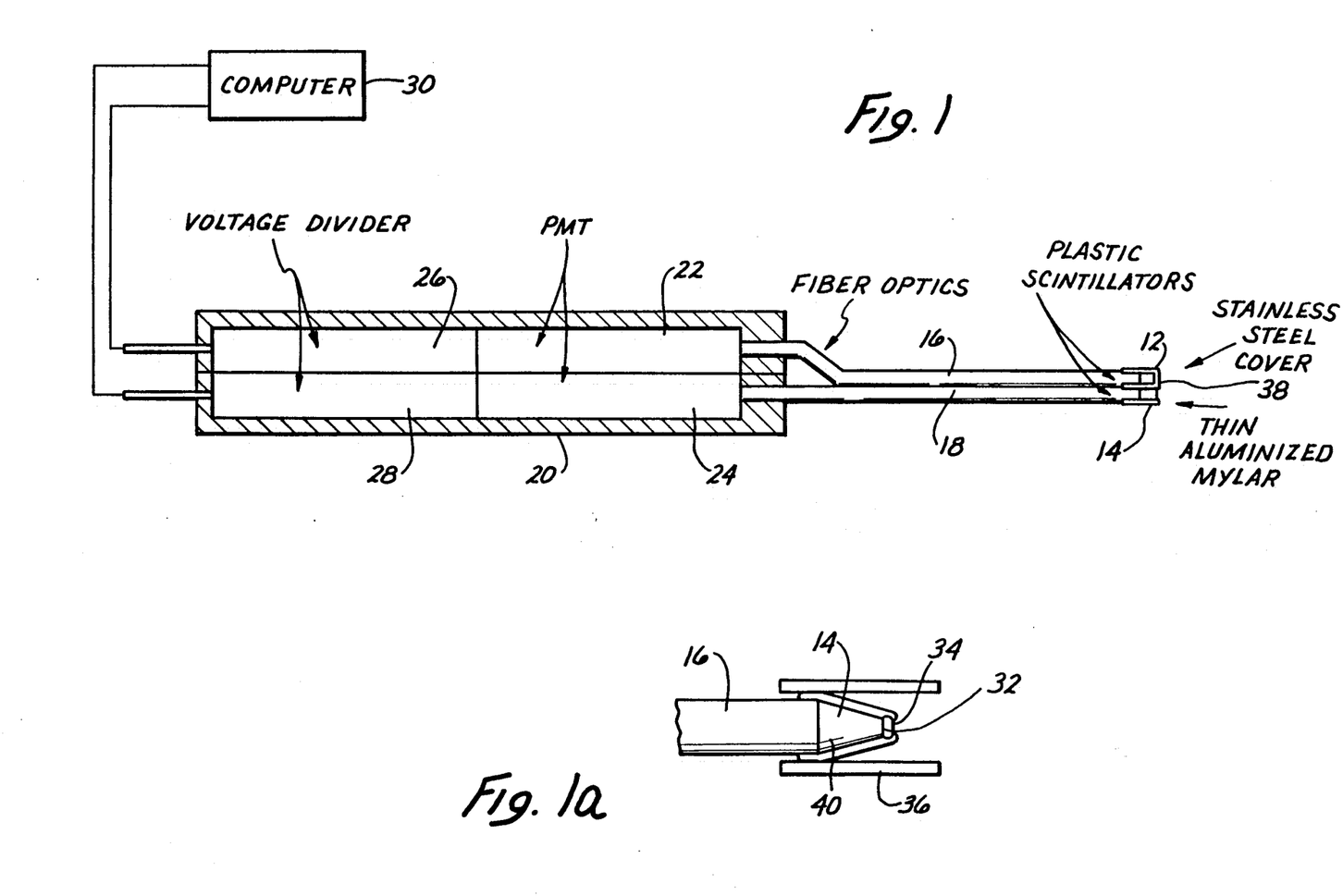
FIG. 1 is a simplified diagrammatic cross-sectional side view of a probe incorporating the invention.
FIG. 1a is an enlargement of the scintillation tip of one of the detectors of FIG. 1.

A simplified cross-sectional side view of the probe of the invention is depicted in FIG. 1. The probe, generally denoted by reference numeral 10, is comprised of two conventional plastic scintillators 12 and 14 coupled to the polished ends of corresponding fiberoptic light pipes 16 and 18 respectively. Fiberoptic light pipes 16 and 18, which may be included within a housing (not shown) for structural rigidity, are led back from scintillators 12 and 14 to a handle or body 20 of probe 10. Fiberoptic light pipes 16 and 18 are optically coupled to corresponding conventional photomultiplier tubes 22 and 24. The electrical output of photomultiplier tubes 22 and 24 in turn is coupled to corresponding conventional voltage dividers 26 and 28 respectively. The output of voltage dividers 26 and 28 are then coupled through conventional interface circuitry provided with a computer 30.

In the preferred embodiment, scintillators 12 and 14 are comprised of plastic scintillating material. The low effective atomic number and density of the plastic scintillator material causes the scintillator to be relatively insensitive to gamma rays. The plastic scintillator is also relatively insensitive to acoustical or vibrational noise, which is a highly desirable characteristic in an operating theater. The scintillator used in the illustrated embodiment is a truncated cone-shaped plastic scintillator with diameters at 2 and 3 mm and a height of 3 mm as manufactured by Bicron Corporation of Newbury, Ohio, Model No. BC400. It must be clearly understood that many other types of plastic scintillating materials or scintillators of completely different compositions as is well known to the art or may become later known could be equivalently employed without departing from the scope of the invention.

Positrons emitted by the radioactive tissue source penetrate the scintillator, collide with an electron and annihilate each other to produce two 511 keV gamma rays with no other particles or radiation. The dominant mode of interaction for the 511 keV gamma rays in plastic is Compton scattering of electrons generally below 340 keV. Therefore, by selectively counting only those events with energies above the Compton edge of approximately 340 keV for annihilation gamma rays generated by all positron emitting isotopes, for example, the probe becomes selectively sensitive to electrons and positrons emitted by the radionuclei.

Turn now to the enlarged sectional view of the probe tip shown in FIG. 1a. Scintillator 14, for example, is provided with a 0.002 inch thick aluminized Mylar foil 34 on end face 32 of scintillator 14. Foil 34 renders the probe light-tight while still allowing beta particles to enter scintillator 14. The remaining side surface or exposed surfaces of scintillator 14 are painted with a 10-micron layer of titanium dioxide to reflect the scintillation light generated within scintillator 14 inward into the body of scintillator 14 and toward light pipe 16. A 0.4 mm-thick gold sleeve 36 is concentrically disposed about scintillator 14 to shield scintillator 14 from stray charges and to form a collimator extending approximately 0.5 mm forward of end surface 32 of scintillator 14.

Scintillator 12 is constructed in a manner identical to that shown in FIG. 1a with respect to scintillator 14 with the exception that scintillator 12 is enclosed within a 1-mm stainless steel cover 38 which may replace sleeve 36 or serves to seal sleeve 36. Stainless steel cover 38 is sufficient to block all electron and positron radiation from entering scintillator 12 which is then exclusively sensitive to gamma rays.

Both scintillators 12 and 14 are coupled at their rear surfaces 40 to a 3-mm diameter light pipe 10 cm. long.

Photomultiplier tubes 22 are approximately 1 cm. in diameter and 5 cm. long and are conventional photomultiplier tubes manufacture by Hamamatsu Corporation of Bridgewater, N.J., Model No. R-1635-02. In the illustrated embodiment computer 30 includes a spectrascopic amplifier, Model TC-203BLR, manufactured by Tennelec to shape and amplify the output of voltage dividers 26 and 28. A single channel analyzer was also included within the circuitry of computer 30, such as a Model 2031 Canberra, to selectively set the energy threshold of photomultiplier tubes 22 and 24.

The threshold voltage of each probe is calibrated by placing each probe before a source of beta and gamma radiation and shielding the probe by a 3 mm-thick piece of copper. The copper will completely absorb the electrons and positrons from the source and only slightly attenuates the gamma rays. The output of the probe is examined to determine its output signal when irradiated only by gamma radiation and then both by beta and gamma radiation. The energy threshold of the probe can be set, if desired, to the point where no gamma radiation will be detected by adjusting the voltage threshold on the photomultiplier tube. This threshold energy varies depending upon the spectrum of the radioisotope utilized as the source and is defined as the Compton edge for the radioisotope.

Figure 4:
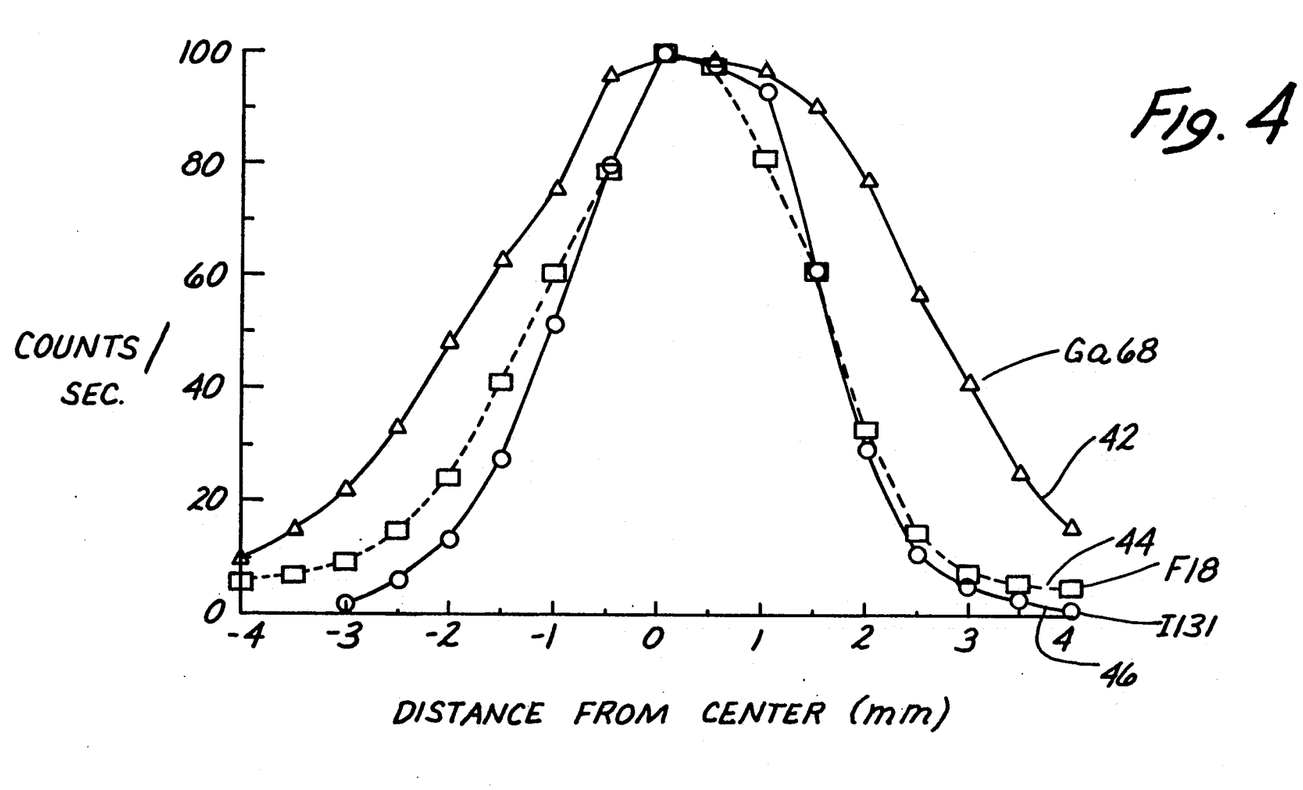
FIG. 4 is a graph showing the spatial resolution of the probe of the invention for three radioisotopes, namely gallium 68, fluorine 18 and iodine 131.

FIG. 4 is a graph which illustrates the spatial resolution of detector 14 of dual probe 10 for different radioisotopes. Curve 42 is the spatial resolution for gallium 68, curve 44 for fluorine 18 and curve 46 for iodine 131. The spatial resolution of FIG. 4 was measured in a phantom specimen depicted in FIG. 2. A single one of the detectors, denoted here as a probe 10', shown in dual configuration in FIG. 1, was provided for the phantom specimen generally denoted by reference numeral 48. The phantom specimen 48 was comprised of a 1×1 cm. Lucite block 50 placed in the bottom of a tank 52. A water-tight plastic bag 54 lines tank 52 and covered block 50. A 2 mm-diameter and 2 mm-deep well 56 was defined in block 50 in which a radioactive solution was placed. Tank 52 lined with plastic bag 54 was then filled with water to simulate surrounding scattering tissue as would be encountered in an intraoperative environment. The end of probe 10' was then covered with a plastic sheath to simulate the sterile plastic covering normally used with the probe in an intraoperative application. The probe was then placed within 1 mm separation from the source within well 56. Block 50 was laterally moved under probe 10' and counts were made for 90 seconds in each lateral position.

Figure 2:
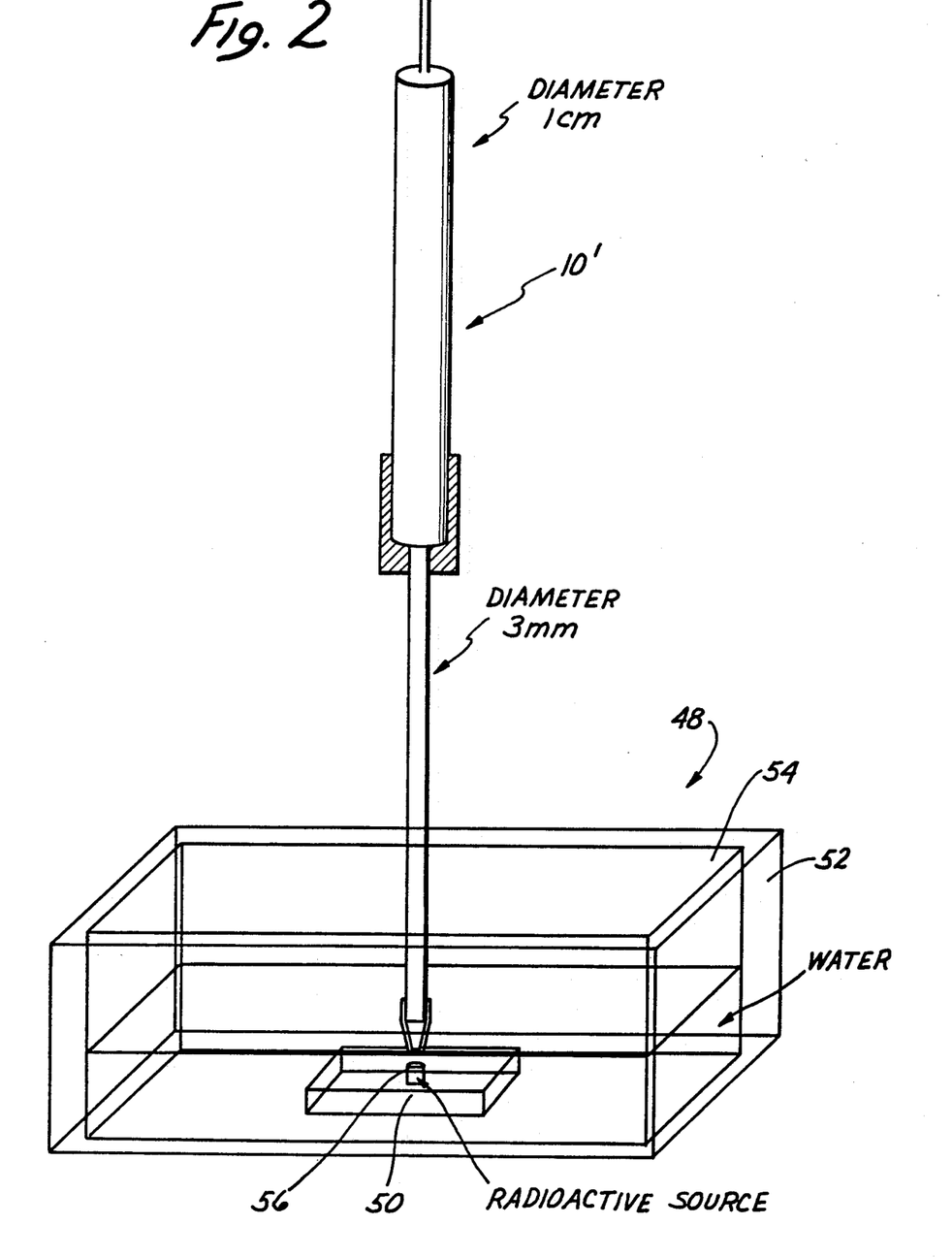
FIG. 2 is a simplified perspective view of a phantom radiation source used to measure the spatial resolution and sensitivity of the probe.

The measured lateral sensitivity of the probe 10' as described in FIG. 2, is graphically illustrated in FIG. 4. Curve 42 for gallium 68 exhibited a full-width-half-maximum of 4.5 mm, fluorine 18 had a full-width-half-maximum of 3 mm and iodine 131 a full-width-half-maximum of 2.5 mm in the illustrated embodiment. Thus the lateral sensitivity of each probe to the half maximum is of the order of one to two times the diameter of the end surface of the corresponding scintillator. Location of the radiolabeled tissue within a few millimeters is easily achieved.

The sensitivity for the three isotopes illustrated in FIG. 4 was measured by placing a nominal 1 microcurie point source within well 56 of block 60. After a series of one-minute measurements, the Lucite block was placed within a well counter and its activity measured. In the illustrated embodiment, the probe showed a sensitivity of 6500 counts per second per microcurie for gallium 68,750 counts per second per microcurie for fluorine 18 and 550 counts per second per microcurie for iodine 131. This sensitivity is consistent with the beta energy spectrum of each of these sources.

The source-to-probe distance in the measurement situation of FIG. 2 was then set to 5 mm. Counts were then collected for 20 seconds for a variety of energy thresholds or voltage potentials applying to the photomultiplier tube both with and without a 2 mm-thick aluminum shield interposed between the source within well 56 and the end of probe 10'. The threshold voltage of the photomultiplier tubes was varied so that the energy threshold measured by the probe varied from zero to the Compton edge of the scintillator. The results are graphically depicted in FIG. 5 for iodine 131.

Figure 5:
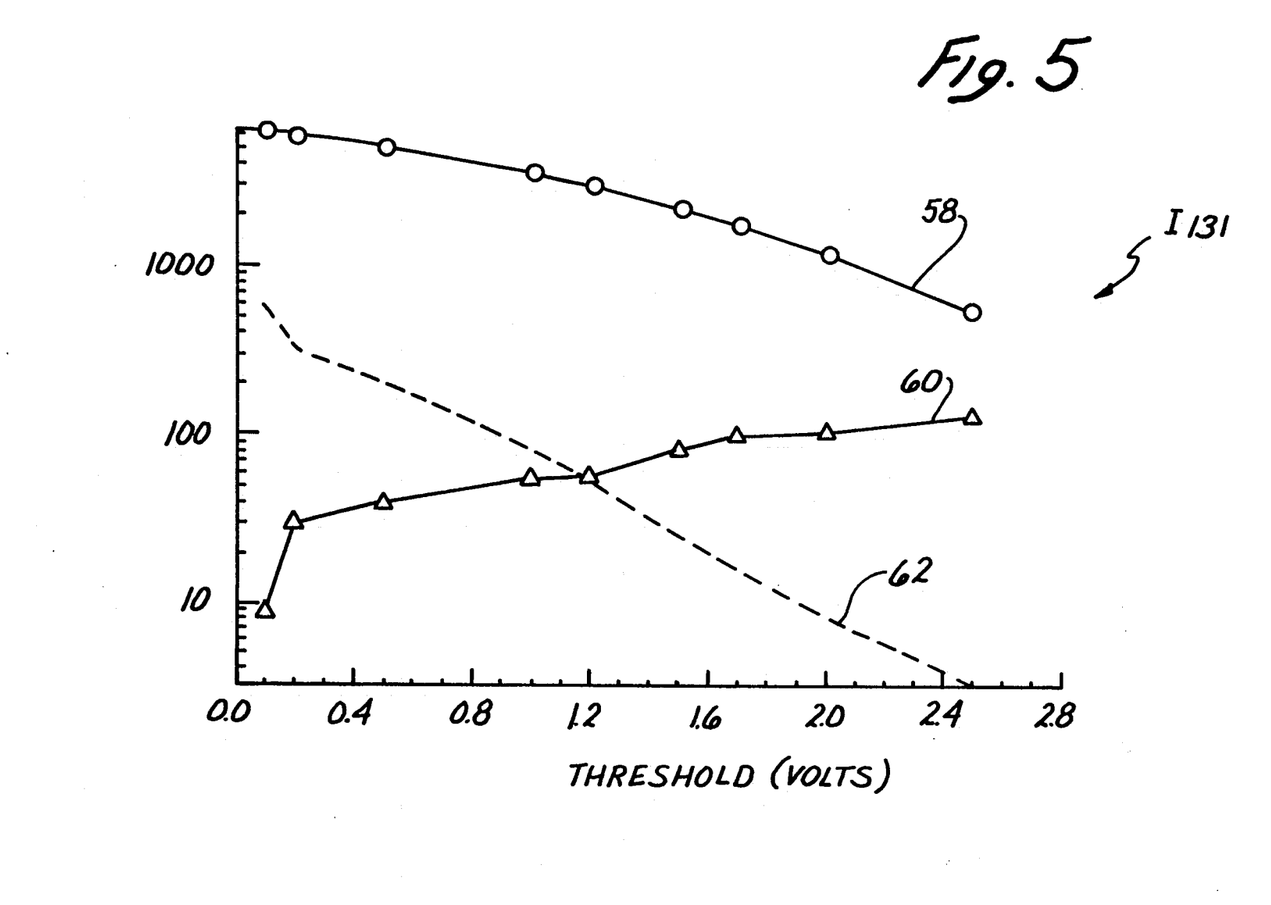
FIG. 5 is a graph showing the sensitivity of the prove for iodine 131, the ratio of beta to gamma efficiency for the probe for iodine 131 and the count rate of the probe when flooded with iodine 131 gamma rays.

Curve 58 represents the sensitivity of the probe measured to nine different energy thresholds drawn on a linear scale on the horizontal axis. The vertical axis of the graph of FIG. 5 is a logarithmic count rate in the case of curve 58. Counts ranged from 6400 counts per second at the lowest threshold energy of 20 keV, to 2200 counts per second at a medium energy threshold of 100 keV, to 550 counts at the highest threshold energy shown on the curve at the Compton edge of 210 keV.

The ratio of beta to gamma efficiencies is also shown in FIG. 5 on curve 60 which ranged from a ratio of 9 at the lowest used energy threshold to 130 at the Compton edge.

Curve 62 of FIG. 5 shows results of flooding the probe with iodine 131 gamma rays. In this case probe 10' was placed 10 cm. away from a 10-millicurie source of iodine 131 radiation enclosed within a glass container. The thickness of the glass container was more than 2 mm and is effective to stop all beta rays while allowing gamma radiation to "flood" the probe. No other attenuating medium was provided between the probe and the flood source. At the Compton edge, the highest energy threshold, 10 counts were recorded in 20 seconds. At the medium and low energy thresholds the count rates were 20 and 560 counts per second respectively.

Thus curve 58 of FIG. 5 represents the total radiation count and curve 62 the gamma count rate, while the ratio between the beta count and the gamma count is shown at curve 60 across a range of threshold values for the photomultiplier tubes. The curve demonstrates that the probe is a more efficient beta counter than gamma counter.

In the dual probe of FIG. 1, the ratio of the gamma ray counts within scintillators 12 and 14 was empirically determined for each selected energy threshold using the gamma ray flooding technique described above. This ratio was 2.2 for the lowest energy threshold of 20 keV which would be the typical operation energy threshold used in intraoperative applications. Other values were obtained at other energy thresholds from which a table could be built and stored within computer 30.

Therefore the counts from scintillator 12, which can see only gamma radiation, is weighted and subtracted from the counts received by scintillator 14, which include both gamma and beta radiation. At a threshold of 20 keV, for example, this weighting factor is 2.2, that is, the count of scintillator 12 is multiplied by 2.2 prior to subtracting from the count of scintillator 14.

The centers of scintillators 12 and 14 are 4 mm apart in the illustrated embodiment. Therefore, the flux of gamma rays from a source 10 cm. away can for all practical purposes be considered identical for both detectors during the gamma flooding. The ratio of gamma counting efficiencies of the two detectors were measured at ten different energy thresholds between the Compton edge and zero. The energy threshold for scintillator 12 was maintained at zero or at a very low level in order to maximize the number of gamma counts recorded. In practice, the energy threshold of both photomultiplier tubes 22 and 24 will be set as low as possible consistent with a good signal-to-noise ratio in order to maximize the number of counts received.

Figure 3:
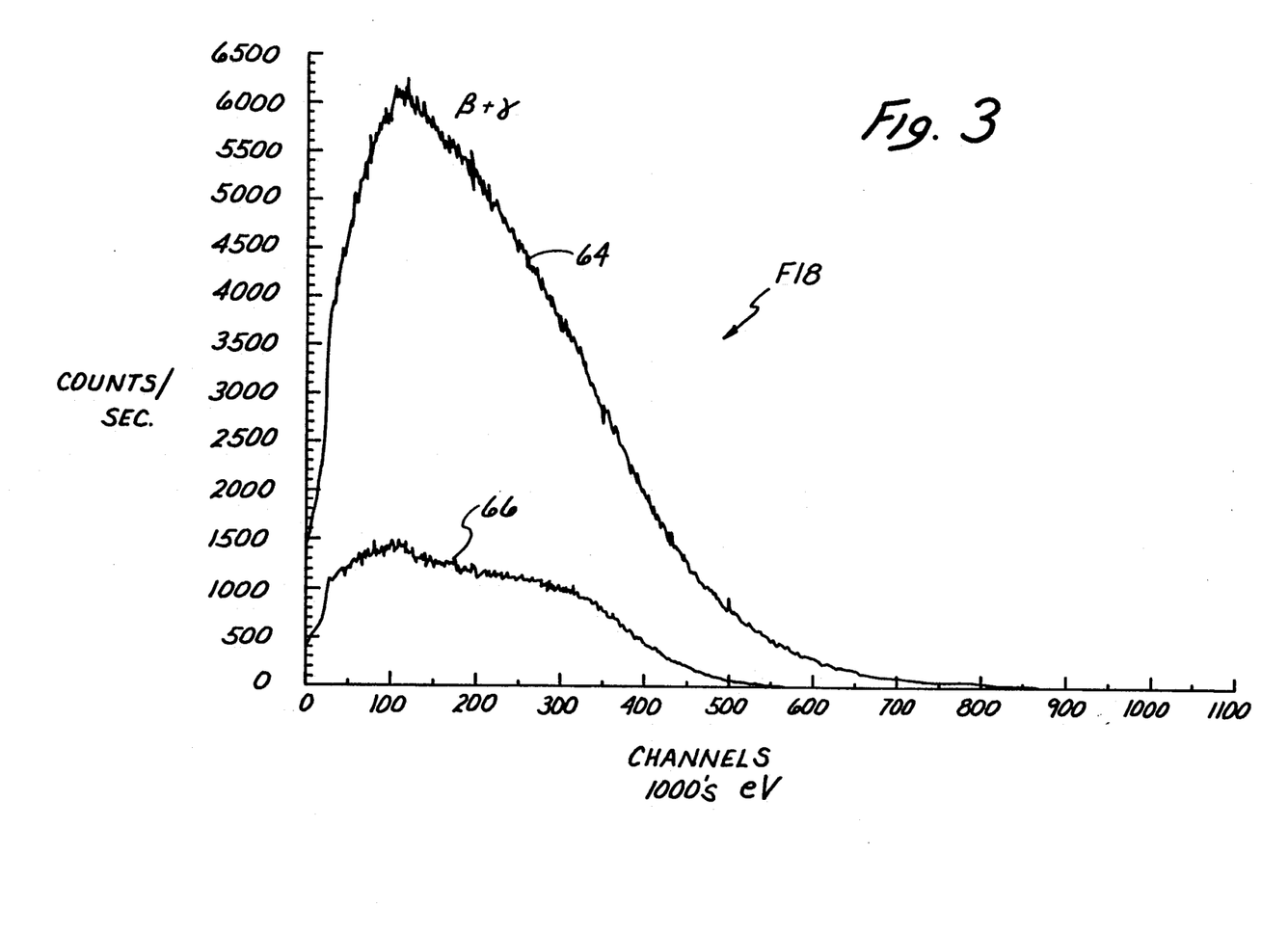
FIG. 3 is the energy spectrum of fluorine 18 as measured by the probe shown in FIG. 2.

FIG. 3 shows the spectrum of the dual probe of FIG. 1 for fluorine 18. Curve 64 is the beta and gamma radiation counts as a function of energy as received by scintillator 14. Curve 66 is the measured number of gamma counts shown as a function of energy as received by scintillator 12. It should be noted that virtually no gamma counts are received above the energy corresponding to channel 550, namely the energy level of the Compton edge for fluorine 18. Therefore, it can be assumed as a practical matter that all counts above channel 550 on curve 64 are due to beta radiation.

It is consistent with the present invention that a single probe could also be utilized as a beta radiation detector if the threshold energy of the detector is adjusted to the Compton edge as symbolized by channel 550 in the graph of FIG. 3.

The count rate above the Compton edge for most markers, such as fluorine 18, is low. Therefore in the preferred embodiment, the threshold of the dual probe will be set as low as possible consistent with the noise-to-signal ratio and weighted subtraction as described above to utilize the full spectrum count of curves 64 and 66 of FIG. 3.

The key advantage of the probe is its ability to exclude distant background radiation in the form of gamma rays while detecting beta radiation with good sensitivity and spatial resolution. In the illustrated embodiment the probe demonstrated an ability to locate a small source of beta radiation and tissue to within a few millimeters. Although some energetic electrons will generate 364 keV gamma rays in scintillators 12 and 14, and while some high energy gamma radiation exists, such as a low intensity 634 keV line in the iodine 131 spectrum, these gamma ray counts do not interfere with locating tumor residues if the radiopharmalogical marker has good selectivity for the tumor.

Although the range of beta rays in tissues limits the depth of detection of the probe to a few millimeters, it must be understood that longer range beta radiation sources such as iodine 124, yttrium 90 and gallium 68 will provide deeper detection ranges. For example, iodine 124 emits positrons at 2.2 and 1.5 MeV. The range of these positrons within tissue is about 1 cm.

For example, assume a patient has been injected with 20 millicuries of iodine 131 in a labelled tumor tracer. In order to detect 10 counts per second with the probe, as described above, when touching a 10-milligram tumor, the tracer must be taken up into the tumor at 0.01% of the injected dose per gram of tumor. This count rate is based on the probe sensitivity as described above with the highest threshold voltage, namely, at the Compton edge of 200 keV for iodine 131. If the probe were readjusted so that energy threshold was set at 90 keV, the 10-milligram tumor would generate 40 counts per second. If the background radiation is simulated by a 10-millicurie gamma ray source 10 cm. away from the probe, then based upon the above study the background gamma count rate in the probe would be 25 counts per second. Therefore, in the illustrated probe used with iodine 131 it can be expected that there can be no difficulty in identifying tumors as small as 10 mg.

Many modifications and alterations can be made by those having ordinary skill in the art without departing from the scope of the invention. For example, in addition to two detectors in a side-by-side configuration, multiple detectors in any geometric configuration and with any geometry of end face can be equivalently used. For example, a concentric arrangement of multiple detectors or any arrangement specifically designed to optimize performance in a given application, which is devised according to the teachings of the invention, could be used. Therefore, the illustrated embodiment has been shown only for the purposes of example and should not be read as limiting the invention or its application as defined in the following claims.

We claim:

1. A probe system for preferentially detecting beta radiation over background gamma radiation from a source of beta and gamma radiation comprising:
   a first means for detecting beta and gamma radiation at an arbitrarily selected location; and
   a second means for selectively detecting only one type of radiation of said beta and gamma radiation, said second and first means coupled together,
   whereby beta radiation from near sources is reliably detected and differentiated from gamma radiation emitted from far sources.

2. The probe system of claim 1 wherein said first means comprises a scintillation detector and said second means comprises a circuit for adjusting the detection threshold energy of said scintillation detector above the Compton edge of said source of beta and gamma radiation.

3. The probe system of claim 1:
   wherein said first means comprises a first scintillation detector arranged and configured to detect beta and gamma radiation from said source; and
   wherein said second means comprises a second scintillation detector for detecting only gamma radiation from said source and means for generating a weighted difference between said outputs of said first and second detectors, said difference being representative of beta radiation detection by said probe system.

4. The probe system of claim 3 wherein said second scintillation detector is identical to said first scintillation detector and further comprises means for shielding said second scintillation detector from beta radiation.

5. The probe system of claim 4 wherein said means for shielding said second scintillation detector is a conductive covering of a predetermined thickness sufficient to absorb substantially all beta radiation emitted by said source.

6. The probe system of claim 2 wherein said scintillation detector comprises:
   a plastic scintillator;
   a light tube optically coupled to said plastic scintillator; and
   circuit means for converting light received through said light tube from said plastic scintillator into an electrical signal.

7. The probe system of claim 3 wherein said scintillation detector comprises:
   a plastic scintillator;
   a light tube optically coupled to said plastic scintillator; and
   circuit means for converting light received through said light tube from said plastic scintillator into an electrical signal.

8. The probe system of claim 5 wherein said scintillation detector comprises:
   a plastic scintillator;
   a light tube optically coupled to said plastic scintillator; and
   circuit means for converting light received through said light tube from said plastic scintillator into an electrical signal.

9. The probe system of claim 6 further comprising means for rendering said plastic scintillator light tight without substantial interference to penetration of beta and gamma radiation into said plastic scintillator.

10. A dual probe system for preferentially detecting beta radiation emitted by radiopharmaceutically marked tissue marked with isotopes emitting beta and gamma radiation in intraoperative surgery comprising:
    a first detector for detecting beta and gamma radiation, said first detector having an output;
    a second detector for detecting gamma radiation, said second detector having an output; and
    means for subtracting a weighted value of said output of said second detector from said output of said first detector to derive a signal indicative of beta radiation detected from said tissue by said dual probe system,
    whereby the location of radioactively tagged tissues may be reliably and accurately identified utilizing beta radiation notwithstanding gamma radiation originating in adjacent tissues.

11. The dual probe system of claim 10 wherein said first and second detectors are scintillation detectors utilizing a plastic scintillator.

12. The dual probe system of claim 11 wherein said first and second detectors further comprise a first and second corresponding photomultiplier tube means for generating an electrical signal in response to an optical input, and light conveyance means for coupling scintillation events within said first and second plastic scintillators to said first and second photomultiplier tube means respectively.

13. The dual probe system of claim 10 wherein said second detector comprises means for shielding said second detector from beta radiation.

14. The dual probe system of claim 13 further comprising means for rendering said first and second detectors light tight without substantially interfering with beta and gamma radiation detection by said detectors.

15. The dual probe system of claim 10 wherein said means for subtracting uses a weighted factor empirically determined by flooding said first and second detector with gamma radiation only and generating a ratio of their respective gamma radiation sensitivities.

16. A method for intraoperatively identifying the location of small masses of radioactively tagged tissues comprising the steps of:
    detecting beta and gamma radiation from said tissue in a first detector;
    simultaneously detecting at substantially the same location gamma radiation from said tissue in a second detector; and
    comparing the amount of beta and gamma radiation detected by said first detector with the amount of gamma radiation detected by said second detector to generate a weighted difference of the amount of radiation detected by said first and second detectors representative of the amount of beta radiation emitted by said tissue, whereby small masses of tissue radioactively tagged with beta and gamma radiation isotopes may be detected near said location of said first and second detectors notwithstanding the presence of gamma radiation from said tissue more distantly located from said location.

17. The method of claim 16 wherein said steps of detecting said beta and gamma radiation and detecting said gamma radiation are performed in said first and second detectors by exposing said first detector to beta and gamma radiation while simultaneously exposing said second detector only to gamma radiation by the step of providing a beta radiation shield for said second detector.

18. The method of claim 17 further comprising the step of shielding said first and said second detectors from light without thereby providing substantial shielding from beta and gamma radiation.

19. An improvement in a method for intraoperatively locating small masses of radioactively tagged tissues in the presence of radioactively tagged distant tissue masses each tagged with a radioactive isotope comprising the steps of:

providing a scintillation detector having a plastic scintillator capable of detecting beta and gamma radiation; and adjusting the threshold energy detectable by said scintillation detector to an energy threshold set at the Compton edge of said radioactive isotope, whereby radioactively tagged near tissue is located notwithstanding the existence of gamma generating radioactively tagged distant tissue.

20. The improvement of claim 19 further comprising the step of rendering said scintillation detector light tight without substantially interfering with detection of beta and gamma radiation by said scintillation detector.

* * * * *